United States Patent [19]

Fedorov et al.

[11] Patent Number: 4,588,406
[45] Date of Patent: May 13, 1986

[54] INTRAOCULAR LENS

[76] Inventors: Svyatoslav N. Fedorov, ulitsa Dostoevskogo, 12, kv. 32.; Eleonora V. Egorova, ulitsa Kuusinena, 15, kv. 41.; Oleg P. Spiridonov, shosse Entuziastov, 100, korpus 5, kv. 108.; Sergei R. Nanushian, ulitsa Stalevarov, 4, korpus 1, kv. 13.; Igor L. Benenson, Karetny ryad, 5/10, kv. 138.; Evgeny I. Degtev, Yaroslavskoe shosse, 14, kv. 34.; Vyacheslav N. Masterov, ulitsa Dubninskaya, 16, korpus 5, kv. 268.; Vladimir G. Kiselev, ulitsa Musorgskogo, 1, kv. 30., all of Moscow, U.S.S.R. 30.1; Vadim Vladimirovich Severny, ulitsa Veshnyakovskogo, 2, kr. 178., all of Moscow, U.S.S.R.

[21] Appl. No.: 766,651
[22] Filed: Aug. 15, 1985
[51] Int. Cl.⁴ ............................................. A61F 2/16
[52] U.S. Cl. ...................................................... 623/6
[58] Field of Search ............................................. 623/6

[56] References Cited
U.S. PATENT DOCUMENTS

Re. 31,640  8/1984  Freeman ................................ 623/6
4,010,496   3/1977  Neefe .................................... 623/6
4,424,597   1/1984  Schlegel ................................ 623/6

FOREIGN PATENT DOCUMENTS 2717706  10/1978  Fed. Rep. of Germany .......... 623/6

Primary Examiner—Richard J. Apley
Assistant Examiner—James Prizant
Attorney, Agent, or Firm—Fleit, Jacobson, Cohn & Price

[57] ABSTRACT

An intraocular lens is disclosed in which the support part is made of a cellular material having closed voids to ensure buoyancy of the lens.

3 Claims, 1 Drawing Figure

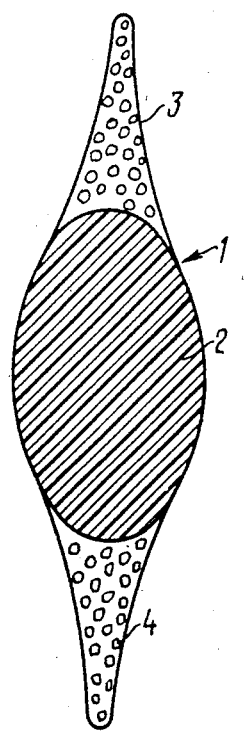

INTRAOCULAR LENS

FIELD OF THE ART

The invention relates to the ophthalmology, and more particularly, it deals with artificial eye lenses which are commonly referred to as intraocular lenses designed for implanting in patients to replace the natural lens upon its extraction in view cataracts of any ethiology or after an eye injury.

BACKGROUND OF THE INVENTION

Various structures of intraocular lenses are known and being used.

Generally they include an optical part made of any optically transparent material biologically neutral with respect to the eye tissues such as glass or polymethyl methacrylate and support (or fastening) members for fixing intraocular lenses in the eye owing to the engagement of the support members with the eye tissues.

The support members are generally made of a thin wire, e.g. a metal wire.

Such intraocular lenses are deficient in that, in spite of the use of wire of a minimum cross-sectional size, their weight is considerable as a substantially heavy weight of the optical part of the lens is added to the weight of the support members. This results in trauma of soft tissues of the eye at points of fastening of the lens and their further degradation during postoperation period. At the same time, it is not possible to make the support members too thin because they will cut into the tissue.

Attempts have been made to replace metal wire with polymeric support members, e.g. of supramid. But such support members also proved deficient because of the weight of the intraocular lens.

All these factors reduce the effectiveness of implantation of intraocular lenses when they remain in the patient's eye for a long time because of degradation of the surrounding tissues and call for new solutions to be sought in designing new intraocular lenses.

Moreover, when wire support members are used, a serious problem arises in developing a process of manufacture of intraocular lenses such that the interconnection of the optical and support parts should not impair quality of the optical member.

SUMMARY OF THE INVENTION

It is an object of the invention to provide an intraocular lens having support members which not only do not apply substantial pressure to soft tissues of the eye at points of engagement with the lens, but are also capable of compensating for the weight of the optical part of the lens.

Another object of the invention is to provide a support member which makes it possible to achieve an easy and reliable connection thereof to the optical part of an intraocular lens so much as to mold the whole lens in the form of a single part in a single production step.

These objects are accomplished by that the support part of an intraocular lens is made of a cellular polymeric material.

If such an intraocular lens is placed in the eye fluid, its weight will be compensated for by buoyancy developed owing to the difference between specific gravities of the fluid and the gas present in closed voids of the cellular material of the support part. This buoyancy will ensure "floating" of the lens.

The advantages of such "floating" lens reside in that pressure of the lens members upon the soft eye tissues at points of engagement with the lens is substantially lowered so that a long-term residence of the implanted lens in the eye will not be accompanied by distrophic changes in the tissues.

By increasing the volume of gas-filled voids, a positive buoyancy may be imparted to such intraocular lenses, which offers new possibilities of sight correction by implanting lenses with injuries of the lower compartment of the eye. This results in a substantial enlargement of the range of medical applications of intraocular eye lenses.

In one embodiment, the material of the support part may be a known per se silicone in which gas-filled voids may be produced using a conventional foaming technique.

The same silicone may also be used for making the optical part of the intraocular lens thus opening radically new ways so that the entire lens may be molded as a single part in a single production step to achieve high quality of the optical part. This also results in a substantial reduction of cost of the lens.

BRIEF DESCRIPTION OF THE DRAWING

The invention will now be described with reference to a non-limiting embodiment of an intraocular lens illustrated in the accompanying drawing showing a sectional view of an intraocular lens according to the invention.

DESCRIPTION OF THE PREFERRED EMBODIMENT

With reference to the FIGURE of drawing, there is shown an intraocular lens according to the invention designated at 1 as a whole and comprising an optical member 2 and a support member 3. The optical member 2 may be made of any optically transparent material which is biologically neutral with respect to the eye tissue and fluid. Such materials may include, e.g. glasses or polymers, in particular polymethyl methacrylate. The choice of material is determined during examination of a patient. The distinctive feature of the invention is the use of an appropriate material for making the support part of the intraocular lens.

As shown in the FIGURE, the support member according to the invention contains a large number of closed gas-filled voids 4. Such voids 4 may be produced using cellular materials for making the support part 3. Such cellular materials may include a cellular polymer, glass or metal, the techniques of making such cellular or foamed materials being well known to those skilled in the art so that they will not be discussed here in detail. It should be noted that cellular materials contain both closed voids or cells and open pores, but it is the presence of the former that is important from the point of view of the invention as they ensure buyancy of the whole lens when placed into the eye fluid. It will be apparent that the number of such voids should depend on the weight of the whole intraocular lens and operation requirements and it may be calculated on the basic of the materials used and their specific gravity values. In particular, we have found that when the whole intraocular lens is made of such biologically neutral material as a silicone, the volume of gas-filled voids in the support part should be within the range of 12 to 15% of the whole volume of the support part and, if the optical part is made of glass and the support part of a cellular silicone, the volume of the gas-filled voids should be increased up to 20-25% of the whole volume of the support part. The optical and support parts may be interconnected easily using known techniques, e.g. hot or solvent welding.

Surgical operations for implanting the "floating" lens are performed using conventional techniques and are determined by the configuration of the support part of the lens and condition of the patient's eye. Thus, the intraocular lens according to the invention may be reliably fixed in the posterior or anterior chamber of the eye. The support members having gas-filled voids may also be used for fixing a lens to the iris of the eye with the same advantages as those inherent in the floating lens.

Use of the invention for correcting sight after extraction of any etiology or eye injuries makes it possible to substantially enlarge the range of medical applications of intraocular lenses and it will be of great help in solving the problem of express and reliable rehabilitation of patients.

What is claimed is:

1. In an intraocular lens comprising an optical part and a support part, an improvement consisting in that the support part is made of a cellular material having substantially closed gas-filled voids in numbers ensuring buoyancy of the lens.

2. An intraocular lens according to claim 1, wherein the material of the optical and support parts is a silicone, the volume of the voids in the support part being 12-15% of the whole volume of the support part.

3. An intraocular lens according to claim 1, wherein the material of the optical part is glass and the material of the support part is a silicone, the volume of the voids in the support part being 20-25% of the whole volume of the support part.

* * * * *